(12) United States Patent
Goudaliez et al.

(10) Patent No.: US 7,766,854 B2
(45) Date of Patent: *Aug. 3, 2010

(54) DEVICE AND METHOD FOR IRREVERSIBLE CLOSURE OF FLUID COMMUNICATION IN A CONTAINER SYSTEM

(75) Inventors: Francis Goudaliez, Faches-Thumesnil (FR); Thierry Verpoort, Mouvaux (FR)

(73) Assignee: MacoPharma, Mouvaux (FR)

( * ) Notice: Subject to any disclaimer, the term of this patent is extended or adjusted under 35 U.S.C. 154(b) by 142 days.

This patent is subject to a terminal disclaimer.

(21) Appl. No.: 11/951,775

(22) Filed: Dec. 6, 2007

(65) Prior Publication Data

US 2008/0132875 A1   Jun. 5, 2008

Related U.S. Application Data

(63) Continuation of application No. 10/217,205, filed on Aug. 12, 2002, now Pat. No. 7,384,416.

(51) Int. Cl.
*A61M 37/00* (2006.01)
*F16K 7/04* (2006.01)

(52) U.S. Cl. .................. 604/6.15; 604/408; 251/10

(58) Field of Classification Search ................ 604/4.01, 604/6.15, 6.16, 415, 407–411, 416, 905, 604/540–541, 317, 19, 164.01, 167.01, 167.03, 604/181, 183, 186, 257, 261, 262, 264, 272, 604/523, 533–7; 128/912, DIG. 24; 422/44

See application file for complete search history.

(56) References Cited

U.S. PATENT DOCUMENTS

| 2,950,716 | A |   | 8/1960 | Walter et al. | 604/409 |
|---|---|---|---|---|---|
| 3,127,892 | A |   | 4/1964 | Bellamy et al. | 604/408 |
| 4,673,161 | A | * | 6/1987 | Flynn et al. | 251/10 |
| 5,167,656 | A |   | 12/1992 | Lynn | 604/409 |
| 5,270,003 | A |   | 12/1993 | Bernes et al. | 422/44 |
| 5,702,383 | A |   | 12/1997 | Giesler et al. | 604/409 |
| 6,123,859 | A |   | 9/2000 | Lee et al. | 210/767 |
| 6,126,618 | A |   | 10/2000 | Bischof | 600/576 |
| 6,328,726 | B1 | * | 12/2001 | Ishida et al. | 604/408 |
| 6,387,086 | B2 | * | 5/2002 | Mathias et al. | 604/409 |
| 6,626,884 | B1 |   | 9/2003 | Dillon et al. | 604/409 |
| 6,692,479 | B2 |   | 2/2004 | Kraus et al. | 604/410 |
| 6,742,760 | B2 |   | 6/2004 | Blickhan et al. | 251/11 |

FOREIGN PATENT DOCUMENTS

EP   1064959 A1   1/2001

OTHER PUBLICATIONS

Notice of Publication of Application for U.S. Appl. No. 10/217,205, filed Jun. 3, 2004.
Office Action for U.S. Appl. No. 10/217,205, filed Sep. 20, 2005.
Office Action for U.S. Appl. No. 10/217,205, filed May 4, 2006.
Office Action for U.S. Appl. No. 10/217,205, filed Dec. 13, 2006.
Office Action for U.S. Appl. No. 10/217,205, filed Aug. 2, 2007.
Notice of Allowance for U.S. Appl. No. 10/217,205, filed Feb. 5, 2008.

* cited by examiner

*Primary Examiner*—Leslie R Deak
(74) *Attorney, Agent, or Firm*—Baker Botts L.L.P.

(57) ABSTRACT

A biological fluid collection system including a collecting device, a collecting container, a first channel connecting the two, a sampling bag, a second channel connecting the sampling bag and the first tube and at least one substantially irreversible closure device in an open position on at least the first or second channel. The biological fluid may be blood. A method of collecting biological fluid such as blood using the system so that fluid in the sampling bag is substantially irreversibly prevented from entering the collecting container.

30 Claims, 2 Drawing Sheets

DEVICE AND METHOD FOR IRREVERSIBLE CLOSURE OF FLUID COMMUNICATION IN A CONTAINER SYSTEM

CROSS-REFERENCE TO A RELATED APPLICATION

This application is a continuation of U.S. patent application Ser. No. 10/217,205 filed Aug. 12, 2002 now U.S. Pat. No. 7,384,416, entitled "Device and Method for Irreversible Closure of Fluid Communication In a Container System," by Francis Goudaliez, et al., which is incorporated by reference herein for all purposes, from which priority is claimed pursuant to 35 U.S.C. §120.

FIELD OF THE INVENTION

The invention concerns a container system including a container for a biological fluid, a channel, and at least one device for substantially irreversible closure of fluid communication within the system. The invention also includes methods of using the system including a method of collecting blood using such a system.

BACKGROUND OF THE INVENTION

Current container systems make it possible to collect blood from a donor or otherwise collect biological fluid. Such systems often include a collecting container, usually a bag, connected to a collecting device by a tube. In addition, the systems may include a sampling container, usually also a bag, intended to receive the first milliliters of blood collected. The sampling container is connected to the tube in such a manner that it is filled after the collecting container is filled.

Filling the sampling bag prior to filling the collecting bag has certain advantages. First, it reduces the risk of contamination of the blood in the collecting bag from bacteria or other foreign substances on the skin of the donor. The first milliliters of blood taken, which are more likely to contain bacteria and foreign substances, are sent into the sampling bag rather than into the collecting bag. Second, use of a sampling bag makes it possible to take samples before the sample or collection bag is completely filled, and consequently not to waste time. Finally, during blood collection, the loss of blood volume for the donor may be compensated for by the addition of plasma. This causes the measured hematocrit of the blood to be lower if the sampling bag is filled, or samples are otherwise taken, after the collecting bag is filled. Consequently, the hematocrit count obtained using such later collected samples may be inaccurate.

After having collected the blood from a donor and before it is transfused into a patient, the blood contained in the sampling bag can be systematically analyzed in order to determine the rhesus group, to effect a hematocrit count and to detect any contamination such as viruses, bacteria or other elements foreign to the blood of the donor.

Although useful, these systems and methods as currently used for collecting blood from a donor do have drawbacks. First, the fact that the closure device situated on the tube connected to the sampling bag can be released could cause it to be opened by the user in order to send the blood remaining in the sampling bag to the collecting bag. This may occur by accident, or through deliberate action, for instance, if the collecting bag is found to be insufficiently filled after disconnection from the arm of the donor. Therefore the reversible closure of the sampling bag tube presents a significant risk of faulty use. This faulty use may negate the contamination containment benefits of the sampling bag and may also lead to other problems.

Moreover, the reversible closure device situated on the tube connecting the needle and the collecting bag does not provide a sufficient seal to be able to dispense with a welder at the location where the blood is collected. Blood collection, particularly at temporary locations, would be more time and cost efficient if welding at the collection location were not required.

SUMMARY OF THE INVENTION

To mitigate these and other drawbacks, the invention includes a container system in which at least one channel connecting its different components is provided with a device for the substantially irreversible closure of fluid communication.

To this end, the invention includes in an exemplary embodiment a container system including a collecting container for a biological fluid such as blood or a blood component.

The collecting container and any other container in the system may be a bag or system of bags, a rigid container, such as a centrifuge well or any other type of container. The collecting container may be selected to serve as a suitable storage container for the biological fluid. The selection of the container may be influenced by the next processing step after collection or by the ultimate use of the biological fluid and other considerations apparent to one skilled in the art.

The collecting container is in fluid communication with a first channel. Such fluid communication may be established through direct connection of the first channel to an inlet/outlet orifice of the collecting container or by any other type of direct or indirect connection known to the art. The first channel and any other channels in the collection system may include a tube or system of tubes, Y joints and other joining structures, or any other device selected based on, inter alia the biological fluid to be collected and its anticipated processing method and uses.

A collecting device for collecting the biological fluid may be provided in fluid communication with the first channel and the collecting bag. The device for collecting the biological fluid may be a needle, a needle assembly, a pump, or another device selected based upon the fluid to be collected and its source or other considerations.

A sampling container is provided in fluid communication with a second channel that is also in fluid communication with the first channel. The sampling container may be a bag, a system of bags, a rigid container or other type of container selected based on, inter alia, the biological fluid, the volume of samples needed, the methods of sampling, and any device used to obtain samples from the sampling container.

A substantially irreversible closure device is provided in or on at least one of the first and second channel. The substantially irreversible closure device may include a locking structure and a flow prevention structure. The substantially irreversible closure device may include a flange and a lock base. It may also be a clamp or a screw. The substantially irreversible closure device may be selected so that, inter alia, when the device is in a closed position, it is not readily restored to an open position without the use of some mechanical device, an unusual or unreasonable amount of force, or some destructive means. In a further example, the substantially irreversible closure device may not be opened by a person of average strength using his or her hands alone.

A device for the reversible closure of the fluid communication may also be provided on the first channel. A sampling device may be associated with the sampling container. One exemplary sampling device is a vacuum tube adapter.

According to a second aspect, the invention includes a method of collecting blood using such a bag system in which the substantially irreversible closure devices are initially open. The method includes the initial step of temporarily closing off the first channel using the reversible closure device. Next blood is collected from a donor in the sampling bag using the collecting device. Then the substantially irreversible closure device provided on the second channel is closed. Next fluid communication is opened in the first channel by maneuvering the reversible closure device, allowing a collection bag to fill with the collected blood. Finally, a substantially irreversible closure device provided on the first channel is closed.

According to a third aspect, the invention is directed to an irreversible closure device, which comprises a lock base including a housing with two lateral clips to allow connection of the device to a tube and at least two internal stops and an intermediate region between the two internal stops and an orifice. The irreversible closure device also includes a flange comprising a projection that presses into the intermediate region between the two internal stops when the flange is closed over the lock base and a finger with a radial toe. The irreversible closure device further includes a hinge around which the lock base and flange rotate with respect to each other. The lock base and flange may be rotated around the hinge to a closed position wherein the finger is disposed within the orifice and is secured therein by the radial toe.

Technical advantages are readily apparent to one skilled in the art from the following figures, descriptions, and claims.

BRIEF DESCRIPTION OF THE DRAWINGS

For a more complete understanding of the invention, and for further features and advantages, reference is now made to the following description, taken in conjunction with the accompanying drawings, in which.

DETAILED DESCRIPTION OF EXEMPLARY EMBODIMENTS OF THE INVENTION

Figure 1:
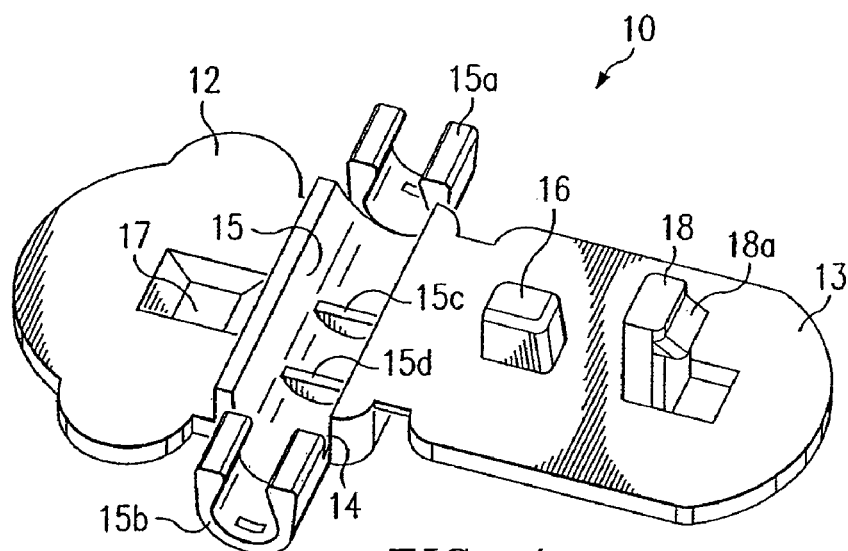
FIG. 1 illustrates, in a perspective view, a device for the irreversible closure of fluid communication through a tube according to the present invention, the device being in the open position.
Figure 2:
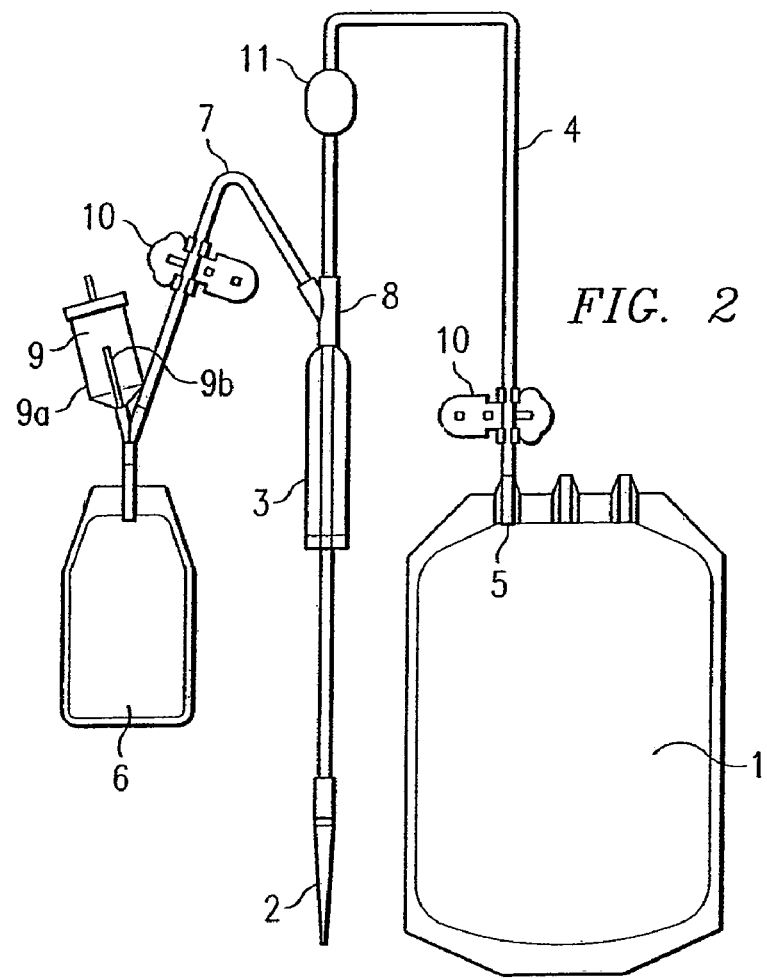
FIG. 2 illustrates, in schematic front view, a bag system according to a first embodiment of the invention.
Figure 3:
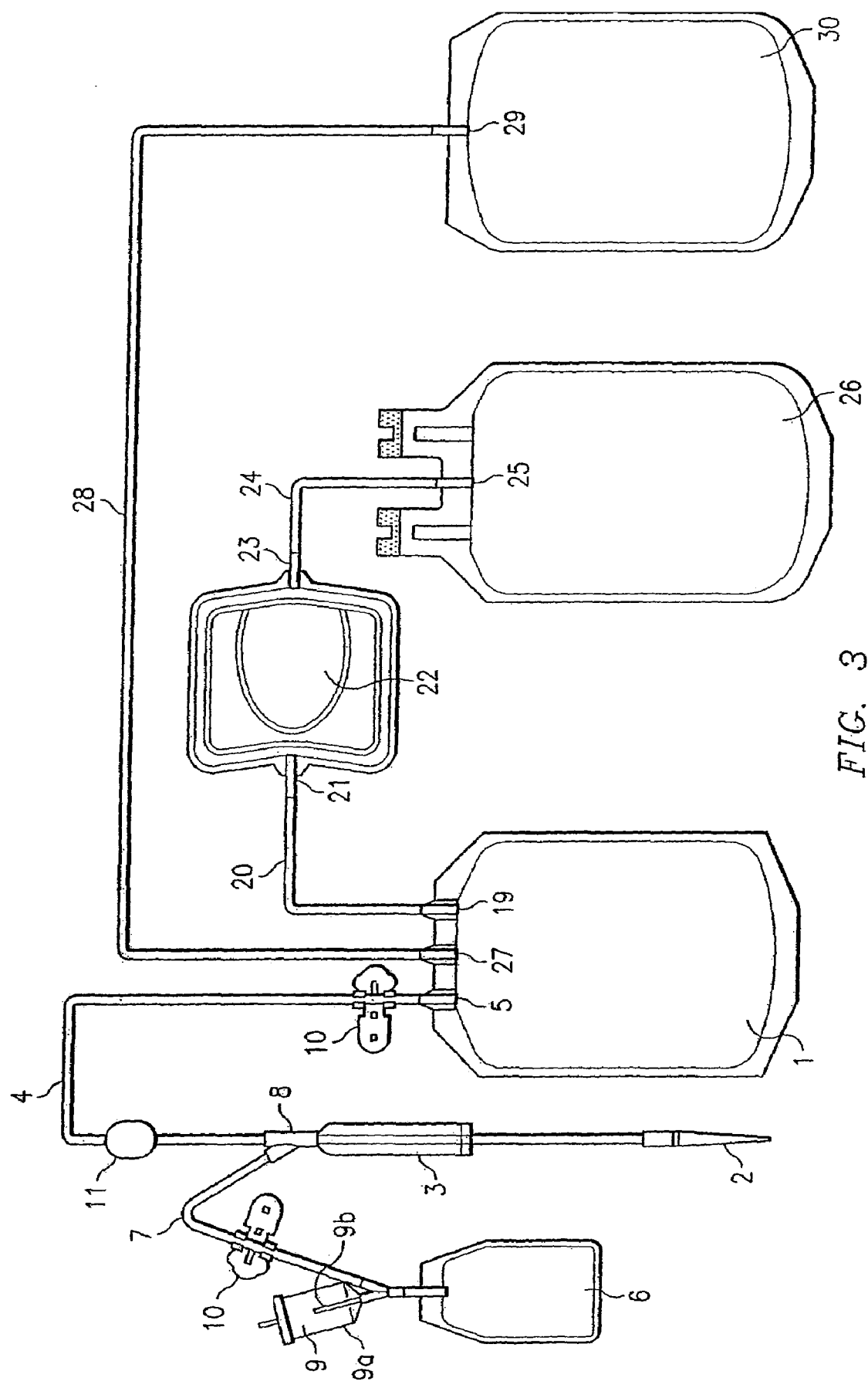
FIG. 3 illustrates, in schematic front view, a bag system according to a second embodiment of the invention.

Exemplary embodiments of the present invention and their advantages are best understood by reference to FIGS. 1 through 3, where like numbers are used to indicate like and corresponding features.

Referring to FIG. 1, an embodiment of a device 10 for the substantially irreversible closure of fluid communication through a channel, such as tube 4 or tube 7 in FIGS. 2 and 3, is described (also referred to as an "irreversible closure device" to effect "irreversible closure").

The irreversible closure device 10 comprises a lock base 12 and a flange 13 mounted for rotation with respect to each other around a hinge 14, between an open position (shown in FIG. 1) and a closed position.

Lock base 12 and flange 13 can be produced from molded plastic material, for example polypropylene, which has the particular property of offering good resistance to steam or beta radiation/sterilization techniques.

Lock base 12 includes housing 15 intended to receive a tube portion. Housing 15 includes two lateral clips 15a, 15b. Clips 15a and 15b are designed so as to allow association of device 10 with a tube in a manner so that device 10, when open, does not substantially restrict fluid communication through the tube. Clips 15a and 15b are additionally designed to assist in holding the tube when device 10 is closed.

Flange 13 includes a projection 16 intended, when device 10 is in the closed position, to crush the tube portion disposed in housing 15, so as to close fluid communication through the tube. For this purpose, projection 16 is provided on the internal face of flange 13 and has a length substantially equal to the depth of housing 15. In addition, the bottom of housing 15 is provided with two stops 15c and 15d which are spaced apart by substantially the width of projection 16 so as, once projection 16 is disposed between stops 15c and 15d, to improve the interruption of fluid communication through the tube.

Lock base 12 and flange 13 include a mechanism for locking device 10 in the closed position that cannot be released manually. For this purpose, lock base 12 includes a female locking mechanism formed by an orifice 17 and flange 13 includes a male locking means formed by a finger 18 provided with a radial toe 18a which is intended to lock on a wall of orifice 17 when finger 18 is inserted therein. Thus, once toe 18a is engaged, it is no longer readily possible to manually disengage finger 18 from the inside of orifice 17.

Referring now to FIGS. 2 and 3, exemplary embodiments of a bag system include a collecting bag 1 intended to contain a biological fluid.

In one example the biological fluid is blood or a blood component such as in particular red cells, possibly concentrated and/or in suspension, blood platelets, possibly concentrated and/or in suspension, blood plasma, possibly with a low or high platelet content.

FIGS. 2 and 3 depict a bag system forming a line for collecting blood from a donor. For this purpose, the system includes a collecting device formed by a needle assembly 2 to be introduced into the vein of a donor and a needle guard 3, the collecting device being provided at one end of a first tube 4 whose opposite end is connected to an inlet orifice 5 to collecting bag 1. In addition the system includes a sampling bag 6 which is connected by a second tube 7 and a Y junction 8 to first tube 4, and a lateral sampling device 9 associated with sampling bag 6 so as to enable samples to be removed by vacuum tubes.

In the embodiments depicted in the figures, first 4 and second 7 tubes are each provided with device 10 for irreversible closure of fluid communication. As a variation, and according to the specific constraints of use of the system, such closure device 10 can be provided solely on one of tubes 4 or 7. In addition, it is also possible to replace other reversible closure devices provided in this or other bag systems with irreversible closure device 10 according to the invention. The system also includes a device 11 for the reversible closure of fluid communication provided on first tube 4, between irreversible closure device 11 and Y junction 8.

Referring now to FIG. 3 alone, the system additionally includes a set of bags intended to separate the different constituents of the collected blood. To this end, collecting bag 1 is connected, at a first outlet orifice 19, to a first end of a tube 20 communicating, through its other end, with an inlet orifice 21 of a filter 22, in particular a deleukocyting filter, allowing the filtration of a whole blood or an erythrocyte concentrate. Filter 22 communicates through its outlet orifice 23 with the first end of a tube 24 communicating, through its second end, with an inlet orifice 25 of a bag 26 for collecting the filtrate. Collecting bag 1 is connected, at a second outlet orifice 27, to a first end of a tube 28 communicating, through its other end, with an inlet orifice 29 of a secondary collecting bag 30.

A description will now be given of one method of collecting blood from a donor using the system depicted in FIG. 1. In this method, two irreversible closure devices 10 are initially open and reversible closure device 11 is closed. Blood is collected using needle 2 inserted into the arm of a donor. Initially, the blood is sent into sampling bag 6 by virtue of the closure of reversible closure device 11 which is situated on first tube 4 and downstream of Y junction 8. When sampling bag 6 is sufficiently filled, irreversible closure device 10 situated on second tube 7 is closed, and then reversible closure device 11 is opened.

The closure of irreversible closure device 10 on second tube 7 eliminates a significant risk of faulty use which could consist, if closure device 10 were not irreversible, of opening it in order to send all or some of the blood contained in sampling bag 6 to collecting bag 1. Such manipulation might allow material caught in the initially drawn blood and secluded in sampling bag 6 to contaminate the blood in collecting bag 1. Additional problems and complications might also result from such faulty use.

During, before or after the filling of collecting bag 1, the user can take samples using sampling tubes and lateral sampling device 9. For this purpose, the user inserts the sampling tubes in a guide tube 9a of sampling device 9 and then, by vacuum the blood is sent from sampling bag 6 to the sampling tube via a sampling needle 9b. One or more sampling tubes may be prepared and used to carry out tests on the collected blood.

When collecting bag 1 is full, the user closes irreversible closure device 10 which is provided on first tube 4. The seal provided by irreversible closure device 10 is sufficient for the user not to be obliged to effect an immediate welding at the collecting location, which presents a significant economic advantage.

In addition, irreversible closure device 10 may be situated close to the vicinity of inlet orifice 5 of collecting bag 1 so as to eliminate or reduce the risk of coagulation in the tubes where anticoagulant is no longer present.

By using instead the system depicted in FIG. 3, the blood collected can then be treated in a conventional manner by centrifugation and filtration so as to separate it into its various constituents. Red cell concentrate may be collected in bag 26 and plasma or plasma constituents may be collected in bag 30 or in a system of bags including bag 30.

Although only exemplary embodiments of the invention are specifically described above, it will be appreciated that modifications and variations of the invention are possible without departing from the spirit and intended scope of the invention.

The invention claimed is:

1. A container system for collection of a biological fluid comprising:
   i) a collecting device;
   ii) a collecting container;
   iii) a first channel providing fluid communication between the collecting device and the collecting container;
   iv) a sampling container;
   v) a second channel providing fluid communication between the first channel and the sampling container; and
   vi) at least one substantially irreversible closure device in an open position provided on at least one of the first and second channels,
      wherein the substantially irreversible closure device, once in a closed position, cannot readily be restored to an open position without using one of a mechanical device, an unreasonable amount of force and a destructive means.

2. The container system of claim 1, wherein biological fluid comprises blood.

3. The container system of claim 1, wherein the collecting device comprises a needle.

4. The container system of claim 1, additionally comprising at least one sampling device operably associated with the sampling container.

5. The container system of claim 1, wherein the substantially irreversible closure device is provided on the second channel.

6. The container system of claim 1, wherein the substantially irreversible closure device is provided on the first channel.

7. The container system of claim 6, wherein the substantially irreversible closure device is provided in close proximity to the collecting container.

8. The container system of claim 1, wherein the system additionally comprises a reversible closure device provided on the first channel.

9. The container system of claim 1, wherein the substantially irreversible closure device comprises a locking structure and a flow-prevention structure.

10. The container system of claim 1, whereby the system is operable to substantially irreversibly close fluid communication in at least one of the first and second channels by manipulation of the substantially irreversible closure device from the open position to a closed position.

11. The container system of claim 1, wherein the substantially irreversible closure device, when closed, prevents fluid from flowing from the sampling container to the collecting container.

12. The container system of claim 1, wherein the first channel comprises a first and second tube.

13. A container system for the collection of a biological fluid comprising:
   i) a means for collecting the biological fluid;
   ii) a means for storing the collected biological fluid;
   iii) a first fluid communication means for providing fluid communication between the means for collecting the biological fluid and the means for storing the collected biological fluid;
   iv) a means for storing initially collected biological fluid for sampling;
   v) a second fluid communication means for providing fluid communication between the first fluid communication means and the means for storing initially collected biological fluid for sampling; and
   vi) at least one means in an open position for substantially irreversible closure of fluid communication in the first or second fluid communication means,
      wherein the means for substantially irreversible closure of fluid communication, once in a closed position, cannot readily be restored to an open position without using one of a mechanical device, an unreasonable amount of force and a destructive means.

14. The container system of claim 13, wherein the biological fluid comprises blood.

15. The container system of claim 13, wherein the system additionally comprises a means of sampling initially collected biological fluid.

16. The container system of claim 13 additionally comprising at least one means for substantially irreversible closure of fluid communication in the first fluid communication means in close proximity to the means for storing the collected fluid.

17. The container system of claim 13, wherein the system additionally comprises at least one means for reversible closure of fluid communication in the first fluid communication means.

18. A container system for the collection of a biological fluid comprising:

i) a collecting container;
ii) a channel in fluid communication with the collecting container; and
iii) at least one substantially irreversible closure device in an open position provided on the channel;
wherein the substantially irreversible closure device, once in a closed position, cannot readily be restored to an open position without using one of a mechanical device, an unreasonable amount of force and a destructive means.

19. The container system of claim 18, additionally comprising a sampling container in fluid communication with the channel and the collecting container.

20. The container system of claim 19, wherein the container system is operable to substantially irreversibly close fluid communication between the sampling container and the collecting container by manipulation of the substantially irreversible closure device from the open position to a closed position.

21. A method of collecting a biological fluid comprising the steps of:
i) closing a reversible closure device provided on a first channel to reversibly close fluid communication within the first channel;
ii) collecting the biological fluid using a collection device so that the biological fluid flows through a portion of the first channel into a second channel in fluid communication with the first channel and into a sampling container;
iii) closing a substantially irreversible closure device positioned on the second channel to close fluid communication within the second channel;
wherein the substantially irreversible closure device, once in a closed position, cannot readily be restored to an open position without using one of a mechanical device, an unreasonable amount of force and a destructive means;
iv) opening the reversible closure device on the first channel so that the biological fluid flows through the first channel into a collecting container.

22. The method of claim 21, additionally comprising the step of closing a substantially irreversible closure device positioned on the first channel to close fluid communication within the first channel.

23. The method of claim 21, wherein the biological fluid is blood.

24. The method of claim 21, additionally comprising the step of obtaining a fluid sample using a sampling device operably associated with the sampling container.

25. An irreversible closure device, comprising:
i) a lock base including:
(a) a housing with two lateral clips to allow connection of the device to a tube and at least two internal stops and an intermediate region between the two internal stops; and
(b) an orifice;
ii) a flange including:
a) a projection that presses into the intermediate region between the two internal stops when the flange is closed over the lock base; and
b) a finger with a radial toe; and
iii) a hinge around which the lock base and flange rotate with respect to each other,
whereby the lock base and flange may be rotated around the hinge to a closed position wherein the finger is disposed within the orifice and is secured therein by the radial toe.

26. A container system for collection of a biological fluid comprising:
i) a collecting device;
ii) a collecting container;
iii) a first channel providing fluid communication between the collecting device and the collecting container;
iv) a sampling container;
v) a second channel providing fluid communication between the first channel and the sampling container; and
vi) at least one substantially irreversible closure device in an open position provided on at least one of the first and second channels,
wherein the substantially irreversible closure device comprises:
a) a lock base including:
(1) a housing for receiving a tube; and
(2) an orifice;
b) a flange including:
1) a projection that presses into the housing and
2) a finger with a radial toe; and
c) a hinge around which the lock base and flange rotate with respect to each other,
whereby the lock base and flange may be rotated around the hinge to a closed position wherein the finger is disposed within the orifice and is secured therein by the radial toe.

27. The container system of claim 26, wherein the substantially irreversible closure device is made of polypropylene.

28. A container system for the collection of a biological fluid comprising:
i) a means for collecting the biological fluid;
ii) a means for storing the collected biological fluid;
iii) a first fluid communication means for providing fluid communication between the means for collecting the biological fluid and the means for storing the collected biological fluid;
iv) a means for storing initially collected biological fluid for sampling;
v) a second fluid communication means for providing fluid communication between the first fluid communication means and the means for storing initially collected biological fluid for sampling; and
vi) at least one means in an open position for substantially irreversible closure of fluid communication in the first or second fluid communication means,
wherein the substantially irreversible closure device comprises:
a) a lock base including:
(1) a housing for receiving a tube comprising
(2) an orifice;
b) a flange including:
1) a projection that presses into the housing and
2) a finger with a radial toe; and
c) a hinge around which the lock base and flange rotate with respect to each other,
whereby the lock base and flange may be rotated around the hinge to a closed position wherein the finger is disposed within the orifice and is secured therein by the radial toe.

29. The container system of claim 28, wherein the substantially irreversible closure device is made of polypropylene.

30. The container system of claim 28, wherein biological fluid comprises blood.

* * * * *